(12) United States Patent
Lee

(10) Patent No.: US 12,214,148 B2
(45) Date of Patent: *Feb. 4, 2025

(54) MULTI-LUMEN DRUG DELIVERY DEVICES AND METHODS

(71) Applicant: TARIS Biomedical LLC, Lexington, MA (US)

(72) Inventor: Heejin Lee, Bedford, MA (US)

(73) Assignee: TARIS Biomedical LLC, Lexington, MA (US)

( * ) Notice: Subject to any disclaimer, the term of this patent is extended or adjusted under 35 U.S.C. 154(b) by 660 days.

This patent is subject to a terminal disclaimer.

(21) Appl. No.: 17/505,897

(22) Filed: Oct. 20, 2021

(65) Prior Publication Data
US 2022/0040461 A1 Feb. 10, 2022

Related U.S. Application Data

(63) Continuation of application No. 16/070,622, filed as application No. PCT/US2017/015122 on Jan. 26, 2017, now Pat. No. 11,185,670.

(60) Provisional application No. 62/287,193, filed on Jan. 26, 2016.

(51) Int. Cl.
*A61M 31/00* (2006.01)
*A61K 9/00* (2006.01)
*A61F 2/04* (2013.01)

(52) U.S. Cl.
CPC ......... *A61M 31/002* (2013.01); *A61K 9/0004* (2013.01); *A61K 9/0034* (2013.01); *A61F 2/042* (2013.01)

(58) Field of Classification Search
CPC ..... A61F 2/042; A61K 9/0004; A61K 9/0034; A61M 31/002
See application file for complete search history.

(56) References Cited

U.S. PATENT DOCUMENTS

| | | | |
|---|---|---|---|
| 4,871,542 A | 10/1989 | Vilhardt | |
| 6,139,535 A | 10/2000 | Greelis et al. | |
| 6,613,025 B1 | 9/2003 | Palasis | |
| 6,629,947 B1 | 10/2003 | Sahatjian et al. | |
| 6,749,617 B1 | 6/2004 | Palasis et al. | |
| 7,288,084 B2 | 10/2007 | Li | |
| 7,762,996 B2 | 7/2010 | Palasis | |
| 8,167,836 B2 | 5/2012 | Lee et al. | |
| 8,182,464 B2 | 5/2012 | Lee et al. | |
| 8,679,094 B2 | 3/2014 | Cima et al. | |
| 8,690,840 B2 | 4/2014 | Lee et al. | |

(Continued)

OTHER PUBLICATIONS

International Search Report and Written Opinion for PCT/US2017/015122, mailed Jul. 3, 2017 (19 pages).

*Primary Examiner* — Brandy S Lee
(74) *Attorney, Agent, or Firm* — Eversheds Sutherland (US) LLP

(57) ABSTRACT

Drug delivery devices are provided herein and include an elongated, elastic body extending between a first end and a second end, wherein the elastic body comprises a water permeable wall structure having defining an elongated drug reservoir lumen extending between the first and second ends. One or more secondary lumens are structured (e.g., positioned, sized, shaped, and optionally filled) to be effective to retard or prevent in vivo diffusion of (i) water into the drug reservoir lumen and/or (ii) solubilized drug out of the drug reservoir lumen.

31 Claims, 6 Drawing Sheets

(56) References Cited

U.S. PATENT DOCUMENTS

| | | | |
|---|---|---|---|
| 8,721,621 B2 | 5/2014 | Boyko et al. | |
| 9,017,312 B2 | 4/2015 | Lee et al. | |
| 9,066,823 B2 | 6/2015 | Ostrovsky et al. | |
| 9,107,816 B2 | 8/2015 | Lee et al. | |
| 9,259,517 B2 | 2/2016 | Li et al. | |
| 9,283,361 B2 | 3/2016 | Dicesare et al. | |
| 9,457,176 B2 | 10/2016 | Lee et al. | |
| 9,492,266 B2 | 11/2016 | Hutchins, III et al. | |
| 9,561,353 B2 | 2/2017 | Lee et al. | |
| 9,586,035 B2 | 3/2017 | Cima et al. | |
| 9,814,671 B2 | 11/2017 | Lee | |
| 10,010,400 B2 | 7/2018 | Lee et al. | |
| 11,185,670 B2 * | 11/2021 | Lee | A61K 9/0034 |
| 2010/0331770 A1 * | 12/2010 | Lee | A61K 9/0034 221/199 |
| 2011/0218488 A1 | 9/2011 | Boyko et al. | |
| 2012/0089122 A1 | 4/2012 | Lee et al. | |
| 2014/0276636 A1 | 9/2014 | Lee et al. | |
| 2015/0088150 A1 | 3/2015 | Lee et al. | |
| 2017/0165460 A1 | 6/2017 | Lee et al. | |

\* cited by examiner

MULTI-LUMEN DRUG DELIVERY DEVICES AND METHODS

CROSS-REFERENCE TO RELATED APPLICATIONS

This application is a continuation of U.S. application Ser. No. 16/070,622, filed Jul. 17, 2018, which is the U.S. national stage application of International Application No. PCT/US2017/015122, filed Jan. 26, 2017, which claims priority to U.S. Provisional Application No. 62/287,193, filed Jan. 26, 2016, all of which are incorporated by reference herein.

BACKGROUND

The present disclosure is generally in the field of in vivo medical devices, and more particularly relates to drug delivery devices for controlled release of drug over an extended period, including but not limited to devices deployable in the urinary bladder for administration of drug into the bladder.

Intravesical drug delivery devices are known. Examples of such devices are described in U.S. Pat. No. 8,679,094 to Cima et al., U.S. Pat. No. 9,017,312 to Lee et al., U.S. Pat. No. 9,107,816 to Lee et al., and U.S. Patent Application Publication No. 2012/0089121 A1 to Lee et al. In some embodiments, the intravesical devices include a water permeable housing defining a drug reservoir lumen which contains a solid or semi-solid drug formulation. In such devices, release of the drug in vivo may occur by water from the bladder diffusing into drug reservoir lumen to solubilize the drug and then an osmotic pressure building up in the drug reservoir lumen to drive the solubilized drug out of the device through a release aperture.

In some cases, e.g., with certain drugs and/or therapeutic applications, it would be desirable to extend the period over which a therapeutic amount of the drug is released and/or to keep the drug from coming out too quickly. One way of accomplishing this is by retarding the rate at which the water can enter the drug reservoir. For example, U.S. Patent Application Publication No. 2009/0149822 to Cima et al. discloses adding a conformal coating or sheath over at least a portion of an outer surface of the housing to reduce the water-permeability of the housing. However, this approach complicates manufacturing. Furthermore, because the device housing of such intravesical devices typically is designed to be elastically deformable, maintaining an effective coating may be challenging, since the coating may delaminate and/or crack during device deformation, which undesirably could alter the drug release kinetics and negatively impact reproducibility of the release profile.

It therefore would be desirable to provide new designs of intravesical drug delivery devices, or other drug delivery devices, capable of releasing drug in vivo at controlled and effective release rates over an extended period, particularly those devices operable as osmotic pump systems or diffusion systems.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale.

DETAILED DESCRIPTION

Figure 1A:
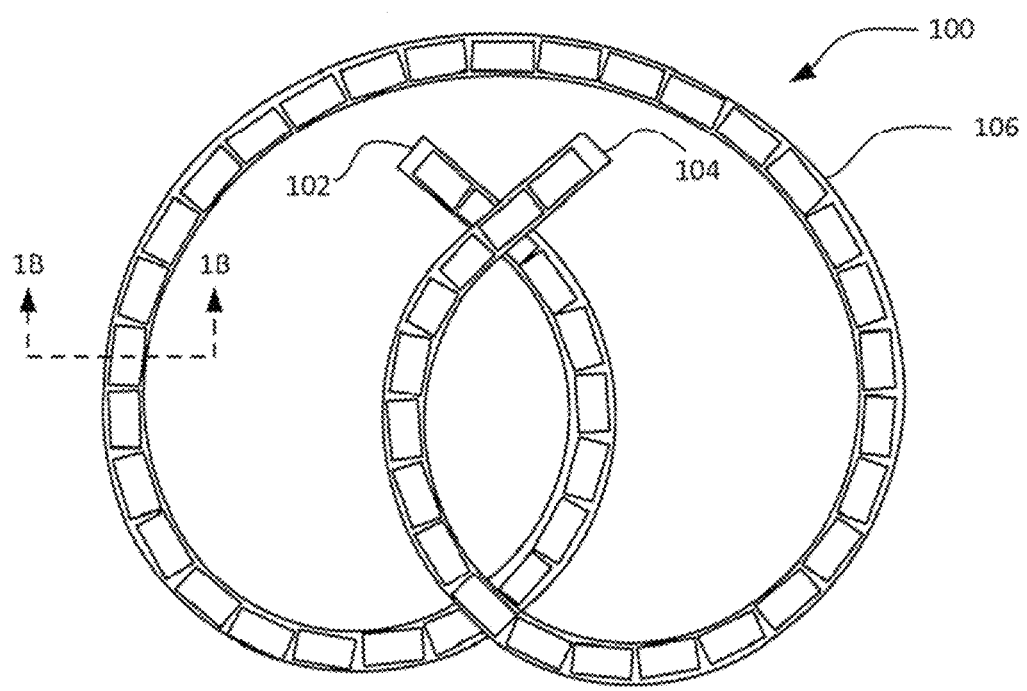
FIG. 1A is a cross-sectional plan view of one embodiment of a drug delivery device in accordance with the present disclosure.

Improved drug delivery devices have been developed, particularly intravesical drug delivery systems having an elastic body or housing containing a drug payload for controlled release by osmotic pumping or trans-wall diffusion.

It is known that the drug release rate from a delivery system that relies on passage of water and/or drug through a tubular device wall can be controlled by the tube wall thickness for a given material. For a diffusion-based system, increased wall thickness means slower drug release through the wall. Similarly, for an osmosis-based system, increased wall thickness means slower osmotic water imbibition through the wall leading to slower drug release. However, because such intravesical tubular drug delivery systems desirably are insertable into the bladder through a deployment instrument placed in a patient's urethra, the available port size for insertion of the drug delivery system is limited by the column strength of the deployment instrument, human anatomy, and patient discomfort associated with a larger size of the instrument. This limitation inevitably affects the maximum allowable cross-sectional size of the drug delivery system. Therefore, the approach of increasing the wall-thickness to slow down drug release cannot be taken beyond a certain point due to the size limitation of the deployment instrument.

An alternative approach to reduce the drug release rate (e.g., compared with that obtained with silicone annular tube) is to screen for alternative materials of construction having suitable water/drug permeability. However, the alternative material with lower permeability also needs to satisfy the mechanical and biochemical property requirements of the device, including biocompatibility, suitable stiffness/ hardness and elasticity to move between a bladder retentive shape and a linear insertion shape, in addition to being effective within the size limitations for device deployment. Such screening is not trivial.

In both approaches (increasing wall thickness and selecting alternative materials), the selected combination of material and wall thickness should impart a device body flexibility that satisfies the shape changing functionality and should not dominate/alter the shape that otherwise would be imparted by a retention frame, such as a nitinol wireform, if used.

Accordingly, new tubular system designs have been developed that can be used with known biocompatible materials of construction, such as silicones, polyurethanes, and ethylene vinyl acetate (EVA), yet provide the desired reduced permeability, mechanical properties, and dimensions suitable for device deployment. In embodiments, the designs reduce trans-wall water imbibition by including areas in the wall structure bounding the drug reservoir that resist trans-wall diffusion of water without impacting the desired mechanical properties and without unduly complicating manufacture of device body. Advantageously, this reduction in trans-wall water imbibition is accomplished without the use of conformal coatings, which may delaminate and/or crack during device use.

The Drug Delivery Devices

In one embodiment, the drug delivery device includes an elongated, elastic body extending between a first end and a second end, wherein the elastic body includes a water permeable wall structure having an external surface and an internal surface defining an elongated drug reservoir lumen extending between the first and second ends; and a drug payload disposed in the drug reservoir lumen, wherein the wall structure includes one or more secondary lumens located between the first and second ends and between the external surface and the drug reservoir lumen. The one or more secondary lumens are structured (e.g., positioned, sized, shaped, and optionally filled) to be effective to retard or prevent in vivo diffusion of (i) water into the drug reservoir lumen and/or (ii) solubilized drug out of the drug reservoir lumen. The wall structure may further include a retention frame lumen in which an elastic retention frame is disposed.

In a preferred embodiment, the one or more secondary lumens are filled with a gas, such as nitrogen, air, or an inert gas. In other embodiments, the one or more secondary lumens are evacuated or filled partially or completely with a diffusion-resistant non-gas material having sufficient fluidity or elastic deformability to not appreciably negate the selected elasticity/stiffness of the overall device imparted by the wall structure, drug payload, and retention frame if present. If the secondary lumen is evacuated, the wall structure needs to be sufficiently rigid so that the lumen remains patent; a collapsed lumen would negate at least in part the diffusion resistance characteristics of the lumen. In an embodiment, the diffusion resistant material is a polymeric material, such as a hydrophobic polymeric material. In still another embodiment, the one or more secondary lumens are filled with a combination of a gas and a non-gas material, for example a composite including a water-insoluble solid and an entrapped gas, e.g., such as in a closed-cell foam. In embodiments which include a non-gas material in the secondary lumen, the non-gas material may be in the form of a film, beads, pellets, coils, or ribbons.

In a preferred embodiment, the one or more secondary lumens are gas-filled and of a large enough size to render the device buoyant in urine in the bladder of the patient. Such buoyancy advantageously can aid in retention of the device in the bladder and may further facilitate the patient's tolerance or lack of notice of the device deployed in the patient. It is particularly advantageous, in certain embodiments, that such gas-filled secondary lumen are separate and distinct from the drug reservoir lumen of the device, yet are positioned about the drug reservoir lumen so that it inhibits diffusion through a significant portion of the wall structure (s) defining the drug reservoir lumen.

In one embodiment, the one or more secondary lumens inhibit diffusion through between 10% and 80%, e.g., between 20% and 70%, or between 30% and 60% of the wall structure(s) defining the drug reservoir lumen. The size, shape, number, and placement of the one or more secondary lumens can vary, and the design considerations of a particular device may drive the selection/design of suitable secondary lumens.

In a preferred embodiment, the water permeable wall structure includes silicone, a polyurethane, ethylene vinyl acetate (EVA), or a combination thereof. In other embodiments, the wall structures may be made of other materials, typically biocompatible polymeric materials.

In a preferred embodiment, the device is elastically deformable between a relatively straightened shape suited for insertion of the device through a urethra and into the urinary bladder of a patient and a coiled retention shape which is suited to retain the device within the urinary bladder.

In one embodiment, the wall structure has a shape which includes an annulus in which the drug reservoir lumen is the central lumen of the annulus and the one or more secondary lumens are defined within one or more portions of the annulus. In one embodiment, the drug reservoir lumen has a circular cross-sectional shape and the one or more secondary lumens have an arcuate, wedge, or crescent cross-sectional shape.

In one embodiment, the wall structure is an elongated, extruded tube having four separate lumens: the drug reservoir lumen, two of the secondary lumens, and a retention frame lumen. In one embodiment, the retention frame lumen and secondary lumens are offset to one side of, and share a common wall with, the drug reservoir lumen. The drug reservoir lumen may have a circular cross-sectional shape and the secondary lumens may each have an arcuate cross-sectional shape. The secondary lumen may take the form of other non-circular shapes besides arcuate shapes.

In a preferred embodiment, the device is operable in vivo to permit water to diffuse into the drug reservoir lumen and solubilize the drug payload and to controllably release solubilized drug from the device by osmotic pressure. In such an embodiment, the drug reservoir lumen is in communication with at least one aperture operable as a release aperture through which solubilized drug is released from the device. The at least one aperture may be defined in the water permeable wall structure, or it may be provided in a plug element closing off an end opening of the drug reservoir lumen.

In another preferred embodiment, the device is operable in vivo to permit water to diffuse into the drug reservoir lumen and solubilize the drug payload and to controllably release solubilized drug from the device by diffusion through the wall structure.

Figure 1B:
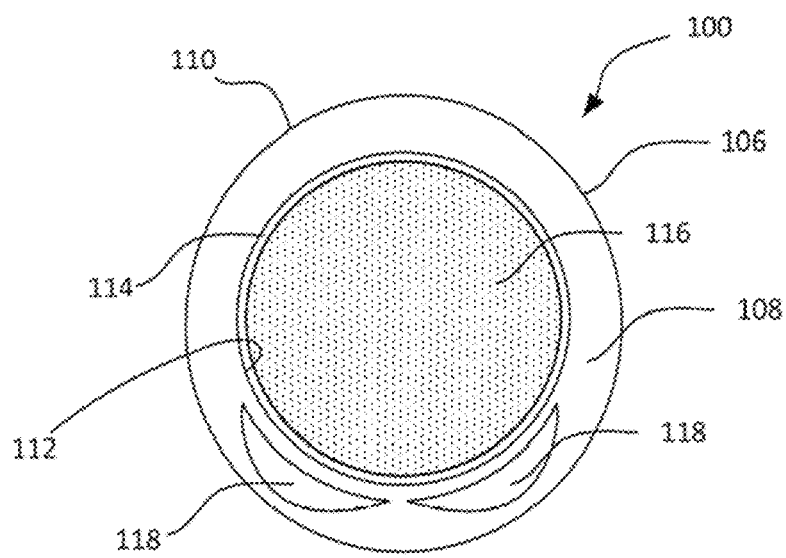
FIG. 1B is a cross-sectional view of the drug delivery device shown in FIG. 1A, taken along line 1B-1B.

One embodiment of the drug delivery devices described herein is shown in FIGS. 1A-1B. The device 100 includes a first end 102, an opposed second end 104, and an elongated, elastic body 106 extending between the first and second ends 102, 104. The elongated body 106 includes a wall structure 108 having an external surface 110 and an internal surface 112 defining an elongated drug reservoir lumen 114. The device 100 further includes a drug payload 116 disposed in the drug reservoir lumen 114. The wall structure 108 includes two arcuate shaped secondary lumens 118 that extend between the first and second ends 102, 104 and that are located in the wall structure 108 between the external surface 110 and the drug reservoir lumen 114. The wall structure 108 has annular shape in which the drug reservoir lumen 114 is the central lumen and the one or more secondary lumens 118 are defined within part of the annulus.

The first and second ends 102, 104 are sealed, with the drug payload loaded within the drug reservoir lumen 114. The first and second ends 102, 104 may be sealed with sealing structures. One or both of the sealing structures may be solid and impermeable to drug. Alternatively, the sealing structures may include a defined through-hole or aperture for drug release by diffusion or osmotic pressure, or the sealing structures may include a drug-permeable wall for drug release by diffusion therethrough.

FIG. 1A shows the device 100 in a coiled retention shape. As used herein, the term "coiled retention shape" generally denotes any shape suited for retaining the device in the intended location within the body that is suited for retaining the device, for example, in the bladder. Similarly, the term "relatively straightened shape" generally denotes any shape suited for deploying the drug delivery device into the body. For example, a linear or elongated shape that is suited for deploying the device through the working channel of a catheter, cystoscope, or other deployment instrument positioned in a lumen of the body, such as the urethra. In embodiments, the drug delivery device may naturally assume the retention shape and may be deformed, either manually or with the aid of an external apparatus, into the relatively straightened shape for insertion into the body. Once deployed the device may spontaneously or naturally return to the initial, retention shape for retention in the body.

In some embodiments, the elongated body itself is configured to provide a retention shape function for the device. That is, the elongated body may be formed of appropriate materials (e.g., a high durometer silicone) and dimensioned to impart the required elasticity and spring constant the device requires. Advantageously, in such embodiments, the elongated body serves the functions of (i) forming the drug reservoir lumen, and (ii) retaining the device in a body cavity (e.g., in the bladder, upon deployment). In an alternative embodiment, the drug delivery device includes an elastic retention frame to provide the retention shape function of the device.

Figure 2:
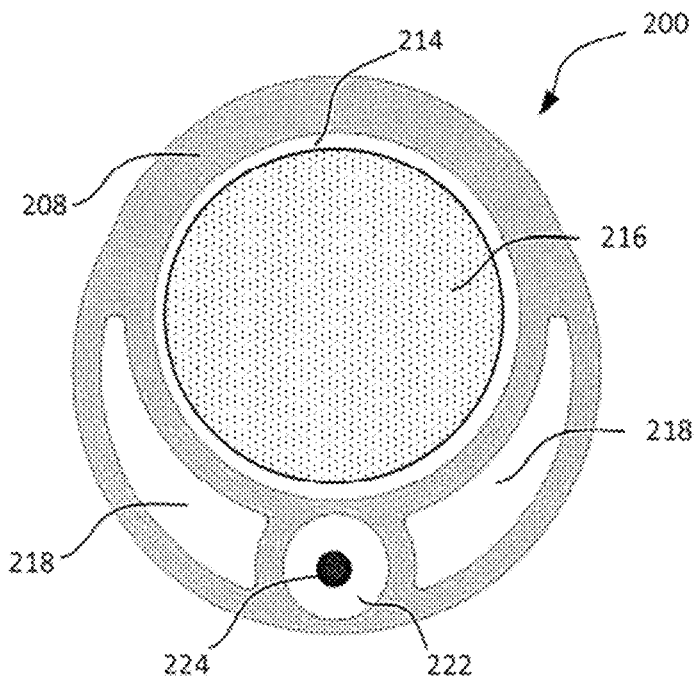
FIG. 2 is a cross-sectional view of another embodiment of a drug delivery device in accordance with the present disclosure.

Another embodiment of the drug delivery devices is shown in FIG. 2. The device 200 includes a wall structure 208 that has two secondary lumens 218 and a retention frame lumen 222 in which an elastic retention frame 224 is disposed. The wall structure 208 also includes drug reservoir lumen 214 in which a drug payload 216 is disposed. The elastic retention frame 224 may be a nitinol wire or other superelastic wire. The elastic retention frame 224 may have an overlapping coiled shape (in the absence of a compressive load) to impart a retention shape to wall structure 208, such that the device 200 has an overall shape like device 100 shown in FIG. 1A. That is, the elastic retention frame 224 is effective to bias the device 200 into a coiled retention shape suited to retain the device 200 within the bladder or another body cavity. For example, the elastic retention frame 224 may have an elastic limit, modulus, and/or spring constant that allows the device 200 to be introduced into the body cavity in a relatively straightened shape, permits the device 200 to return to the retention shape once inside the body (e.g., immediately upon release from a deployment instrument which applies a compressive load onto the device to temporarily hold device 200 in the relatively straightened shape), and impedes the device 200 from assuming the relatively straightened shape within the body in response to expected forces. Such a configuration may limit or prevent accidental expulsion of the device from the body under expected forces. For example, the device may be retained in the bladder during urination or contraction of the detrusor muscle.

In another embodiment of a design for reducing trans-wall water imbibition, the drug delivery device includes a device body that is an elongated, extruded tube with three or more separate lumens: a centrally located retention frame lumen, and a drug reservoir lumen and one or more secondary lumens radially disposed around the retention frame lumen. In one case, the drug reservoir lumen and two secondary lumens are each offset to one side of, and share a wall with, the retention frame lumen, while simultaneously sharing a common wall with each other (see, e.g., FIGS. 5A-B, further described below). In another case, the drug reservoir lumen and a secondary lumen are each offset to one separate side of, and share a wall with, the retention frame lumen, while simultaneously sharing two common walls with each other (see, e.g., FIG. 6, further described below).

In various embodiments, the drug reservoir lumen and the secondary lumen each may have various cross-sectional shapes. In one case, one or more of the lumen are cylindrical in shape. In another case, the cross-sectional shape is non-cylindrical, for example, being defined by a combination of one or more curved walls and one or more straight walls. For example the non-cylindrical lumen illustrated in FIGS. 5A-B may be considered wedged shaped.

Figure 5A:
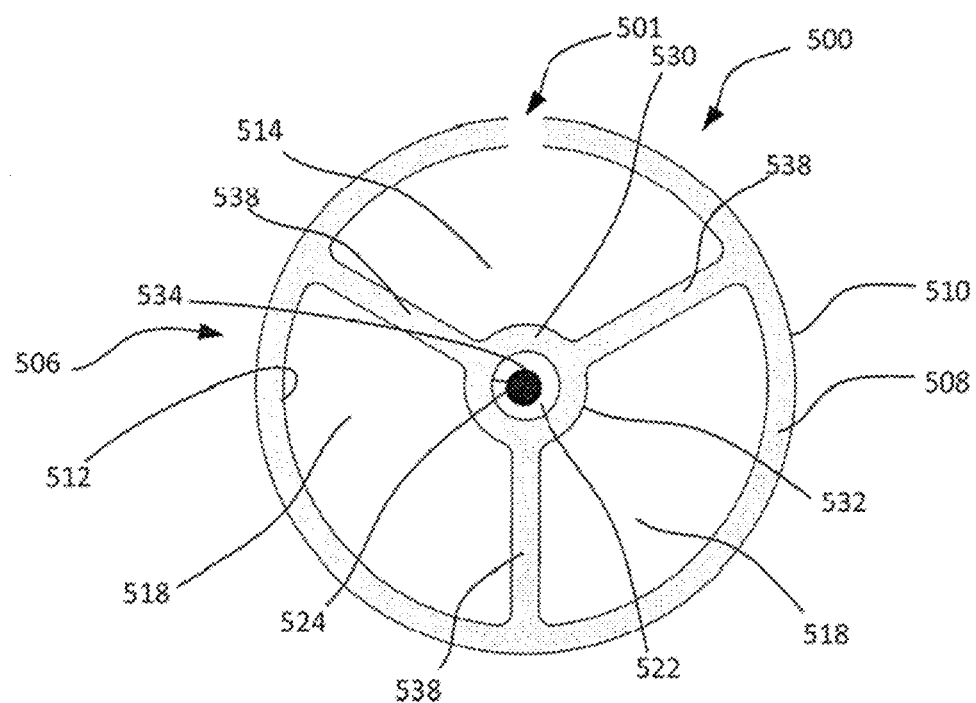
FIGS. 5A-5B are cross-sectional views of another embodiment of a drug delivery device, without a drug payload (FIG. 5A) and with a drug payload (FIG. 5B), in accordance with the present disclosure.
Figure 5B:
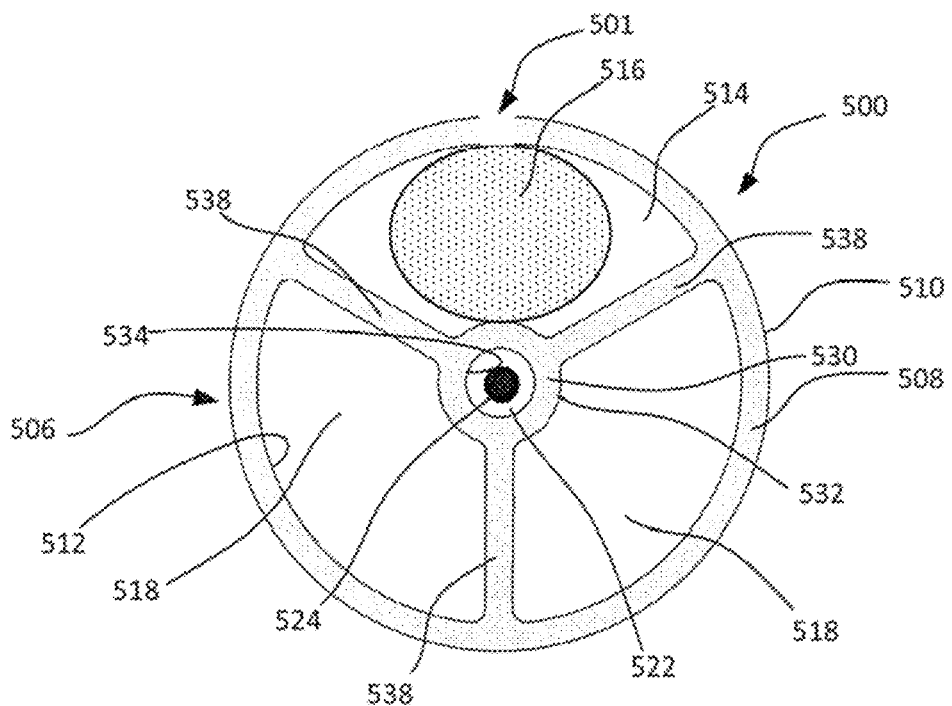
Figure 7:
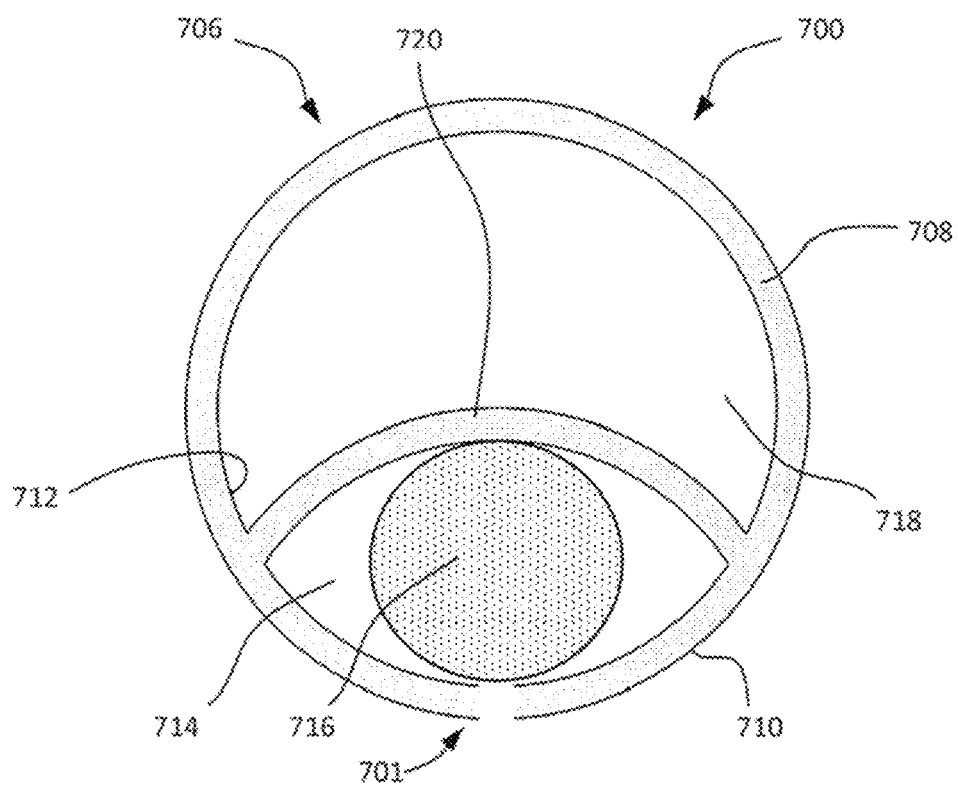
FIG. 7 is a cross-sectional view of another embodiment of a drug delivery device in accordance with the present disclosure.
Figure 8:
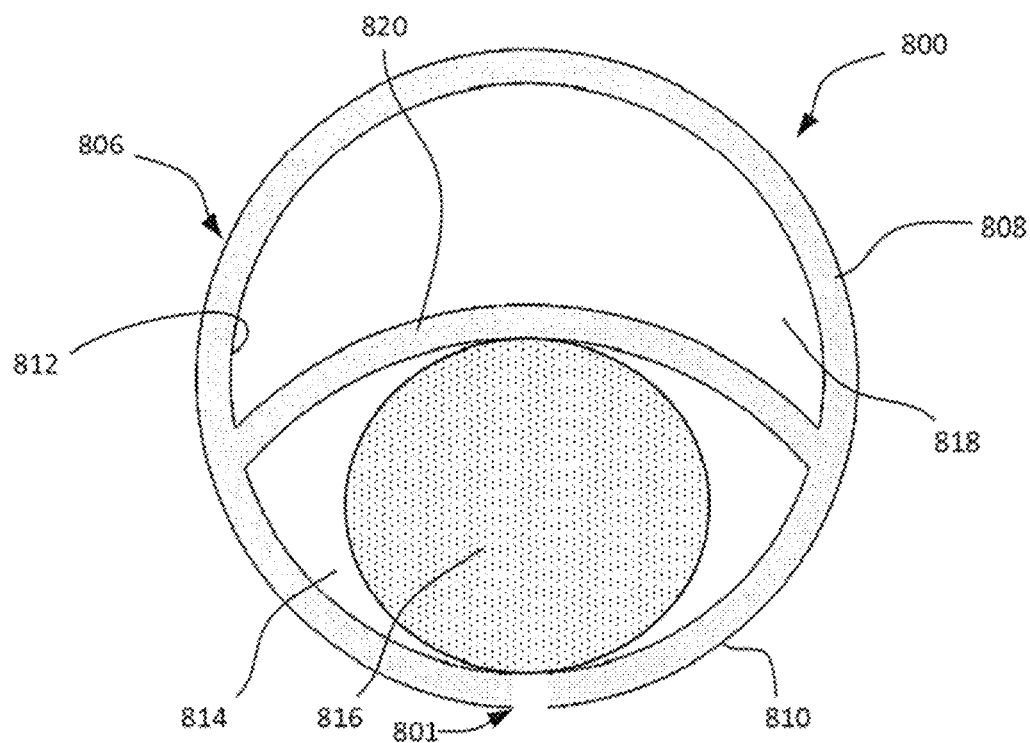
FIG. 8 is a cross-sectional view of yet another embodiment of a drug delivery device in accordance with the present disclosure.

A wedge-shaped or other non-cylindrical shaped drug reservoir lumen may be advantageous to use with cylindrical solid drug tablets, because such a combination may provide additional gas-filled spaces around the drug tablets (as illustrated in FIG. 5B, FIGS. 7-8) to further increase device buoyancy when in use in the bladder, which may contribute desirably to the retention of the device within the bladder and to tolerability of the device in the bladder (from the patient's perspective). In one embodiment, the elastic nature of the wall structures defining the drug reservoir lumen permits elastic deformation of the lumen such that a drug payload of substantially circular solid drug tablets may be readily secured within a non-cylindrical drug reservoir lumen. In this case, the circumference and the perimeter of the tablets and the interior surface of the lumen are close enough to have no significant gas-filled space. In a preferred embodiment, the drug delivery device, with a non-cylindrical reservoir, has a cylindrical outer shape so that the device can readily be deployed through cylindrical working channels of various cystoscopes, catheters, and inserters suitable for intravesical deployment of the drug delivery devices.

In another embodiment of a design for reducing trans-wall water imbibition without impacting the desired mechanical properties and without unduly complicating manufacture of device body, the drug delivery device includes an elongated, elastic body extending between a first end and a second end, wherein the elastic body includes a water permeable first wall structure having an external surface and an internal surface defining an elongated drug reservoir lumen extending between the first and second ends; and a drug payload disposed in the drug reservoir lumen, wherein the elastic body includes a second wall structure which in part defines one or more secondary lumens located between the first and second ends and located between the second wall structure and the first wall structure. The one or more secondary lumens (air lumen) again are effective to retard or prevent in vivo diffusion of (i) water into the drug reservoir lumen and/or (ii) solubilized drug out of the drug reservoir lumen.

Figure 3:
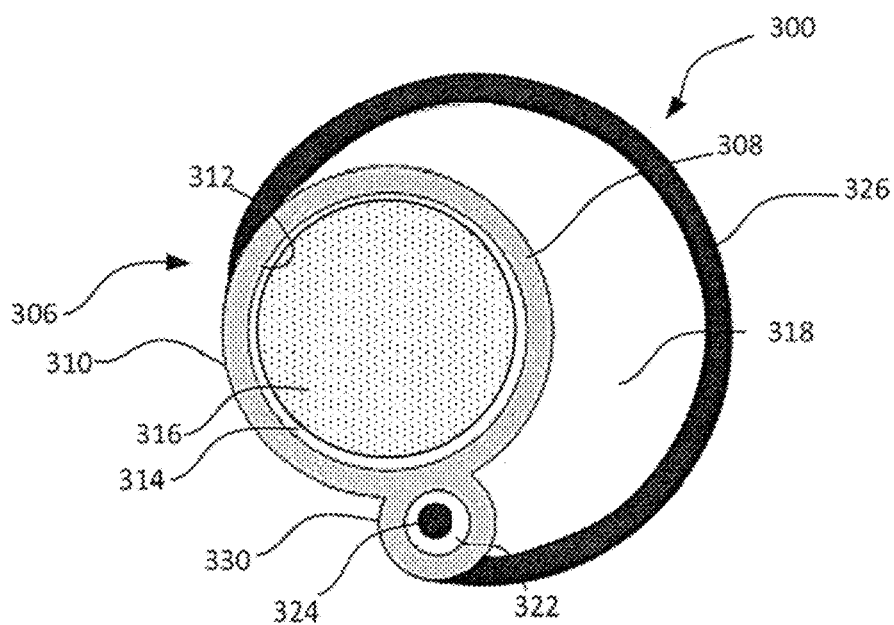
FIG. 3 is a cross-sectional view of still another embodiment of a drug delivery device in accordance with the present disclosure.

Another embodiment of the described drug delivery devices is shown in FIG. 3. Drug delivery device 300 includes an elongated elastic body 306 that extends between a first end and an opposed second end of the device. The elongated body 306 includes a first wall structure 308 having an external surface 310 and an internal surface 312. The internal surface 312 defines an elongated drug reservoir lumen 314. A drug payload 316 is disposed within the drug reservoir lumen 314. The first wall structure 308 further includes a retention frame lumen 322 in which an elastic retention frame 324 is disposed. The elongated elastic body 306 of drug delivery device 300 further includes a second wall structure 326 that extends between the first and second ends of the device. The second wall structure 326 is an elongated, extruded C-shaped tube segment connected to, and offset to one side of, the first wall structure 308. The second wall structure 326 is attached to the first wall structure 308 in a manner such that the first and second wall structures 308, 326 together define a secondary lumen 318. The secondary lumen 318 is located between the second wall structure 326 and the drug reservoir lumen 314. The first and second wall structures 308, 326 may be formed separately and then attached together, or alternatively, they may be co-extruded and formed simultaneously.

In an alternative embodiment (not shown), the first and second wall structures are configured to form two or more separate secondary lumens. For example, the embodiment show in FIG. 3 could further include a wall portion approximately bisecting the secondary lumen 318 and extending between outer surface 310 of first wall structure 308 and the interior wall of second wall structure 326 providing additional structural support to maintain the patency of the secondary lumen.

The exact arrangement and relative sizes of the first and second wall structures 308, 326 are selected to control the portion of the external wall surface 310 that is exposed for water imbibition and the portion of the external wall surface 310 that is shielded by the secondary lumen 318. In the illustrated embodiment, the drug reservoir lumen 314 has a circular cross-sectional shape and the secondary lumen 318 has a non-circular cross-sectional shape. In alternative embodiments, these cross-sections can have different shapes. In a preferred embodiment, the overall outer cross-sectional shape of the device (i.e., the combination of the first and second wall structures) is substantially circular.

The retention frame lumen 322 is defined by a retention frame luminal wall 330. In the illustrated embodiment, the retention frame luminal wall 330 is part of the first wall structure 308. In an alternative embodiment (not shown), the retention frame luminal wall is part of the second wall structure 326, instead of the first wall structure 308. In still another embodiment (not shown), the retention frame luminal wall 330 is form by a combination of the first and second wall structures.

The first and second wall structures 308, 326 may be formed of the same or different materials of construction. In a preferred embodiment, the water permeable first wall structure includes silicone, a polyurethane, ethylene vinyl acetate (EVA), or a combination thereof. In other embodiments, the first wall structure may be made of other materials, typically biocompatible polymeric materials. The second wall structure preferably is also made of a biocompatible elastic polymer. It may be, but need not be water permeable. The second wall structure 326 may be formed of a material having a higher durometer value than the first wall structure 308. In one embodiment, the second wall structure also includes silicone, a polyurethane, ethylene vinyl acetate (EVA), or a combination thereof. In a preferred embodiment, the second wall structure is formed from a high durometer silicone. A high durometer silicone may beneficially aid in maintaining the patency of the secondary lumen. As used herein, a "high durometer" polymeric material means one having a hardness from Shore 75 A to Shore 88. In other embodiments, the first or second wall structure is formed of a polymer having a durometer value from 45 Short A to 88 Shore A.

The one or more secondary lumens may be non-cylindrical, such as the arcuate lumens illustrated in FIGS. 1-3. In other embodiments, however, the one or more secondary lumens are cylindrical.

FIGS. 5A-5B illustrate, in cross-section, a drug delivery device 500, which may be used for controlled release of a drug into the urinary bladder of a patient. The device 500 includes an elongated, elastic body 506 extending between a first end and an opposed second end. The elastic body includes a water permeable outer wall structure 508 having a cylindrical shaped external surface 510 and internal surface 512. The wall structure 508 extends between the first and second ends of the device. The device 500 further includes an elongated hub structure 530 located within, and coaxial with, the outer wall structure 508 and extending between the first and second ends. The device 500 includes three spoke structures 538 extending between and connecting the outer wall structure 508 and the hub structure 530. The three spoke structures 538, the cylindrically-shaped outer wall structure 508, and the hub structure 530 define an elongated drug reservoir lumen 514 and two air lumens 518. The spoke structures 538 aid in maintaining the patency of the drug reservoir lumen 514 and the two air lumens 518. FIG. 5B shows a drug payload in the form of at least one solid drug tablet 516 loaded in the drug reservoir lumen 514. In a preferred embodiment, the device 500 is elastically deformable between a relatively straightened shape suited for insertion of the device through a urethra and into the urinary bladder of the patient and a coiled retention shape which is suited to retain the device within the urinary bladder. As illustrated, the hub structure 530 has an annular shape with an exterior surface 532 and an interior surface 534, wherein the annulus defines a retention frame lumen 522, in which an elastic retention frame 524 is disposed. In an alternative embodiment (not shown), the hub structure is solid (i.e., has no lumen). In one variation of this alternative, the hub structure is polymeric and shape set to impart the coiled retention shape to the device.

As illustrated in FIGS. 5A-5B, the three spoke structures 538 extend from the hub structure 530 at positions equally spaced from one another, such that each pair of spoke structures bounding one of the lumen defines an angle of 120 degrees. In one variation on this design, the three spoke structures may be positioned to define an obtuse angle bounding each of the drug reservoir lumen and the two air lumen, but the angles need not be equal. In other variations, one or two of the angles may be acute, or one of the angles may be obtuse.

Figure 6:
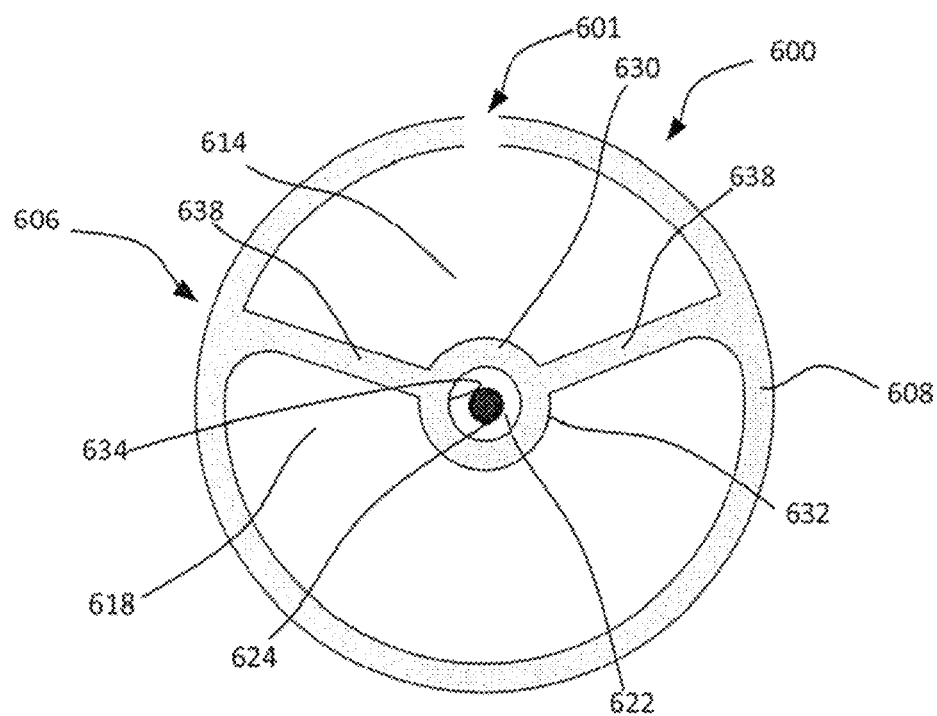
FIG. 6 is a cross-sectional view of still another embodiment of a drug delivery device in accordance with the present disclosure.

FIG. 6 illustrates, in cross-section, a drug delivery device 600, which may be used for controlled release of a drug into the urinary bladder of a patient. It is similar to device 500, but has two, instead of three, spoke structures. The device 600 includes an elongated, elastic body 606 extending between a first end and an opposed second end. The elastic body includes a water permeable outer wall structure 608. The wall structure 608 extends between the first and second ends of the device. The device 600 further includes an elongated hub structure 630 located within, and coaxial with, the outer wall structure 608 and extending between the first and second ends. The device 600 includes two spoke structures 638 extending between and connecting the outer wall structure 608 and the hub structure 630. The two spoke structures 638, the outer wall structure 608, and the hub structure 630 define an elongated drug reservoir lumen 614 and an air lumen 618. A drug payload (not shown) which also may be in the form of at least one solid drug tablet would be loaded in the drug reservoir lumen 614. In a preferred embodiment, the device 600 is elastically deformable between a relatively straightened shape suited for insertion of the device through a urethra and into the urinary bladder of the patient and a coiled retention shape which is suited to retain the device within the urinary bladder. As illustrated, the hub structure 630 has an annular shape with an exterior surface 632 and an interior surface 634, wherein the annulus defines a retention frame lumen 622, in which an elastic retention frame 624 is disposed. In an alternative embodiment (not shown), the hub structure is solid (i.e., has no lumen) and may be polymeric and shape set to impart the coiled retention shape to the device.

As illustrated in FIG. 6, the two spoke structures 638 extend from the hub structure 630 at positions to define an obtuse angle bounding the drug reservoir lumen and a reflex angle bounding the air lumen. In one variation on this design (not shown), the two spoke structures may be positioned within the same plane, such that the spoke structures extend in opposite directions. In this way, the angle bounding each of the drug reservoir lumen and the air lumen is 180 degrees. In another variation (not shown), the two spoke structures extend from the hub structure at positions to define a reflex angle bounding the drug reservoir lumen and an obtuse angle bounding the air lumen.

In one embodiment, the outer wall structure 508 or 608 adjacent the drug reservoir lumen 514 or 614 includes a drug release orifice 501 or 601, which may be used in an osmotic pumping system. For instance, the device may be configured to be operable in vivo to permit water to diffuse into the drug reservoir lumen and solubilize the drug payload and to controllably release solubilized drug from the device by osmotic pressure, through an orifice in the outer wall structure adjacent to the drug reservoir lumen. In such an embodiment, the outer wall structure adjacent the drug reservoir lumen would be of an elastomeric material and thickness that is water permeable but substantially impermeable to the solubilized drug.

In another embodiment, the device is operable in vivo to permit water to diffuse into the drug reservoir lumen and solubilize the drug payload and to controllably release solubilized drug from the device by diffusion. The angle selected and therefore the area of the outer wall bounding the drug reservoir lumen illustrated in FIGS. 5A-B and FIG. 6 may be selected, for example, based on the degree to which the one or more air lumens are needed to retard or prevent in vivo diffusion of (i) water into the drug reservoir lumen and/or (ii) solubilized drug out of the drug reservoir lumen.

In the embodiments illustrated in FIGS. 5A-B and FIG. 6, the spoke, outer wall, and hub structures may be coextruded and integrally connected, or alternatively, one or more of these structures may be formed separately and then joined/attached to the other structures. The spoke, outer wall, and hub structures may be formed of the same or different materials of construction. In a preferred embodiment, the structures are all formed of a biocompatible polymeric material, such as polyurethane or silicone. Other suitable elastomers are also envisioned.

Figure 9:
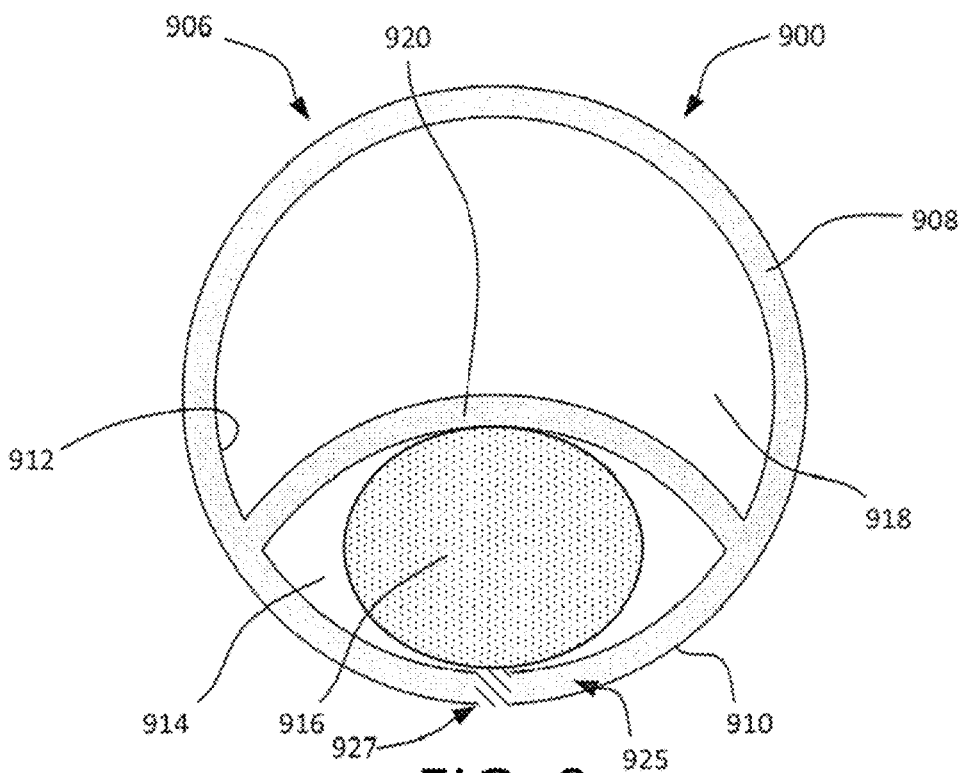
FIG. 9 is a cross-sectional view of a further embodiment of a drug delivery device in accordance with the present disclosure.

Further embodiments of drug delivery devices for controlled release of drug into the urinary bladder of a patient are illustrated in FIGS. 7-9.

FIG. 7 shows device 700 which includes an elongated, elastic body 706 extending between a first end and a second end, wherein the elastic body includes an outer wall structure 708 having an external surface 710 and an inner surface 712, wherein the outer wall structure 708 has an annular shape and extends between the first and second ends. The elastic body 706 further includes an arcuate interior wall structure 720 extending across the annulus of the outer wall structure 708 and connected to the interior surface 712 of the outer wall structure 708 in a manner that defines within the annulus an elongated, biconvex drug reservoir lumen 714 on one side of the interior wall structure 720 and a crescent shaped air lumen 718 on a second side of the interior wall structure 720. A drug payload 716 is disposed in the drug reservoir lumen 714. In this embodiment, the drug payload, which includes a drug, is in the form of a plurality of solid drug tablets (the cross-section of one is shown) which are cylindrical in shape. (The drug may alternatively be in other solid forms (e.g., powders, capsules, beads) or semi-solid or liquid forms.) The drug tablets may be loaded relatively easily into the biconvex shaped drug reservoir lumen 714 due to the elastic (elastomeric) nature of the outer and interior wall structures, which, for example, may be made of silicone, ethylene vinyl acetate (EVA), and/or polyurethane. The initial biconvex shaped drug reservoir lumen 714 can be deformed into near circular shape, being left no unfilled space, if circumference of the drug tablet significantly matches the biconvex inner bounds of drug reservoir lumen 714.

FIG. 8 shows device 800 which is very similar to device 700, except that the arcuate interior wall structure is positioned differently within/across the annulus of the outer wall structure, such that in device 800, the drug reservoir lumen is larger and the air lumen is smaller. In this way, the area of the outer wall bounding the drug reservoir lumen is greater in device 800 than in device 700. Device 800 includes an elongated, elastic body 806 extending between a first end and a second end, wherein the elastic body 806 includes an outer wall structure 808 having an external surface 810 and an inner surface 812. The outer wall structure 808 has an annular shape and extends between the first and second ends. The elastic body 806 further includes an arcuate interior wall structure 820 which extend across the annulus of the outer wall structure 808 and connects to the interior surface 812 of the outer wall structure 808 in a manner that defines within the annulus a biconvex, elongated drug reservoir lumen 814 on one side of the interior wall structure 820 and a crescent shaped air lumen 818 on a second side of the interior wall structure 820. A drug payload 816 is disposed in the drug reservoir lumen 814. The initial biconvex shaped drug reservoir lumen 814 can be deformed into near circular shape, being left no unfilled space, if circumference of the drug tablet significantly matches the biconvex inner bounds of drug reservoir lumen 814.

In embodiments, devices 700 and 800 are elastically deformable between a relatively straightened shape suited for insertion of the device through a urethra and into the urinary bladder of the patient and a coiled retention shape which is suited to retain the device within the urinary bladder. In particular embodiments, the device includes an elastic retention frame to provide the coiled retention shape. In one embodiment, the elastic retention frame is disposed in the air lumen.

In one embodiment, the outer wall structure 708 or 808 adjacent the drug reservoir lumen 714 or 814 includes a drug release orifice 701 or 801, which may be used in an osmotic pumping system. For instance, the device may be configured to be operable in vivo to permit water to diffuse into the drug reservoir lumen and solubilize the drug payload and to controllably release solubilized drug from the device by osmotic pressure, through an orifice in the outer wall structure adjacent to the drug reservoir lumen. In such an embodiment, the outer wall structure adjacent the drug reservoir lumen would be of an elastomeric material and thickness that is water permeable but substantially impermeable to the solubilized drug.

In another embodiment, the device is operable in vivo to permit water to diffuse into the drug reservoir lumen and solubilize the drug payload and to controllably release solubilized drug from the device by diffusion. One embodiment includes the ones in FIG. 7 or FIG. 8, where drug loaded in the drug reservoir lumen can diffuse predominantly through the bottom side wall defining the biconvex lumen. The air lumen 718 or 818 limits diffusion of the drug out of the drug reservoir lumen 714 or 814.

Another example of such an embodiment is illustrated in FIG. 9, which shows a device 900 which is similar to device 800. Device 900 includes an elongated, elastic body 906 extending between a first end and a second end, wherein the elastic body 906 includes an outer wall structure 908 having an external surface 910 and an inner surface 912. The outer wall structure 908 has an annular shape and extends between the first and second ends. The elastic body 906 further includes an arcuate interior wall structure 920 which extend across the annulus of the outer wall structure 908 and connects to the interior surface 912 of the outer wall structure 908 in a manner that defines within the annulus a biconvex, elongated drug reservoir lumen 914 on one side of the interior wall structure 920 and a crescent shaped air lumen 918 on a second side of the interior wall structure 920. A drug payload 916 is disposed in the drug reservoir lumen 914. The outer wall structure 908 is formed of two different materials of construction: A first material portion 925 which is impermeable to the drug when the drug is in solution and a second material portion 927 which is permeable to the drug when the drug is in solution.

In one embodiment, following insertion of the device 900 into the bladder of a patient, water from the urine diffuses through portion 925 (and likely through portion 927 too) and into the drug reservoir lumen 914, solubilizes at least a portion of the drug payload (when initially in a solid or semi-solid form) to form a drug solution, and then the drug solution diffuses out of the device 900 through portion 927 and into the urine in the bladder for subsequent diffusion into/through the urothelium. The air lumen 918 limits diffusion of the water into the drug reservoir lumen 914, such that little or no water enters the drug reservoir lumen 914 through interior wall 920.

The first and second material portions 925, 927 may be formed together and integrally connected, for example by an extrusion process. These portions may be formed from a variety of suitable materials, for example silicone, polyurethane, ethylene-vinyl acetate (EVA), thermoplastic silicone polyether polyurethane, aliphatic thermoplastic silicone polyether polyurethane, segmented polyether polyurethane, thermoplastic polyether polyurethane, thermoplastic polycarbonate polyurethane, Bionate® PCU, BioSpan® SPU, CarboSil® TSPCU, Elasthane™ TPU, PurSil® TSPU (DSM), other thermoplastic polyurethanes (TPUs), including aliphatic and aromatic, polycarbonate-based thermoplastic polyurethanes, such as Carbothane™ TPU, Tecoflex™ TPU, Tecothane™ TPU, Pellethane® TPU, and Tecophilic™ TPU, and combinations or blends thereof.

The drug permeable portion 927 may be a hydrophilic polymer, for example hydrophilic polyurethane, hydrophilic polyesters, and hydrophilic polyamides. In one embodiment, the drug permeable wall structure is Tecophilic™ thermoplastic polyurethane, HydroThane™ thermoplastic polyurethane (AdvanSource Biomaterials Corp.), Quadraphilic™ thermoplastic polyurethane (Biomerics, LLC) (ALC grades are aliphatic polycarbonate-based and ALE grades are aliphatic polyether-based hydrophilic polyurethanes), HydroMed™ (AdvanSource Biomaterials Corp.), or Dryflex® (HEXPOL TPE). Another hydrophilic polymer that may form the drug permeable portion is polyether block amide Pebax® MV 1074 SA 01 MED (Arkema), which is a thermoplastic elastomer made of flexible and hydrophilic polyether and rigid polyamide.

The air lumens in devices 700, 800, and 900 may be filled with air, nitrogen, an inert case, or other material suitable for retarding diffusion of water into the drug reservoir lumen, as described herein with respect to the other embodiments of the drug delivery device.

In the embodiments illustrated in FIGS. 7-9, the outer wall and interior wall structures may be coextruded and integrally connected, or alternatively, one or more of these structures may be formed separately and then joined/attached to the other structures. The interior and exterior wall structures may be formed of the same or different materials of construction. In a preferred embodiment, the structures are formed of one or more biocompatible polymeric materials, such as polyurethane, silicone, ethylene-vinyl acetate (EVA), or a combination thereof. Other suitable elastomers are also envisioned.

The length of the elongated body of the devices described herein may be selected depending upon a variety of factors including the specific site of deployment, route of insertion, drug, dosage regimen, and therapeutic application of the device. In one embodiment, the elongated body is from 10 cm to 15 cm in length. In embodiments, the material used to form the elongated body, at least in part, may be elastic or flexible to permit the device between a relatively straightened shape and a retention shape. The elongated body may be formed of elastic material or materials having the necessary modulus or spring constant required to bias the device into a retention shape.

In embodiments, the drug delivery devices may be sized and shaped to fit through a narrow tubular path of a deployment instrument, such as a catheter or cystoscope. The devices may be inserted into a patient using a cystoscope or catheter. Typically, a cystoscope for an adult human has an outer diameter of about 5 mm and a working channel having an inner diameter of about 2.4 mm to about 2.6 mm. In embodiments, a cystoscope may have a working channel with a larger inner diameter, such as an inner diameter of 4 mm or more. Thus, the devices may be relatively small in size. For example, when the devices are elastically deformed to the relatively straightened shape, the devices for an adult patient may have a total outer diameter that is less than about 2.6 mm, such as between about 2.0 mm and about 2.4 mm. For pediatric patients, the dimensions of the devices are anticipated to be smaller, e.g., proportional for example based on the anatomical size differences and/or on the drug dosage differences between the adult and pediatric patients. In addition to permitting insertion, the relatively small size of the devices may also reduce patient discomfort and trauma to the bladder.

The devices also may be small enough in the retention shape to permit intravesical mobility. In particular, the devices when deployed may be small enough to move within the bladder, such as to move freely or unimpeded throughout the entire bladder under most conditions of bladder fullness, facilitating patient tolerance of the device. Free movement of the devices also facilitates uniform drug delivery throughout the entire bladder.

The elongated body of the devices described herein can be made to be completely or partially bioerodible so that no explantation, or retrieval, of the devices is required following release of the drug. In some embodiments, the device is partially bioerodible so that the device, upon partial erosion, breaks into non-erodible pieces small enough to be excreted from the bladder. As used herein, the term "bioerodible" means that the device, or part thereof, degrades in vivo by dissolution, enzymatic hydrolysis, erosion, resorption, or combinations thereof. In one embodiment, this degradation occurs at a time that does not interfere with the intended kinetics of release of the drug from the device. For example, substantial erosion of the device may not occur until after the drug is substantially or completely released. In another embodiment, the device is erodible and the release of the drug is controlled at least in part by the degradation or erosion characteristics of the erodible device body.

Drug Payload

The drug payload contains one or more drug formulations. The drug formulation may consist only of a drug, or the drug formulation may include the drug and one or more excipients. That is, the drug formulation may include a drug content and an excipient content.

The drug may be essentially any therapeutic, prophylactic, or diagnostic agent. In a preferred embodiment, the drug payload includes one or more active pharmaceutical ingredients (APIs). As used herein, the term "drug" with reference to any specific drug described herein includes its alternative forms, such as salt forms, free acid forms, free base forms, and hydrates. The drug may be a small molecule drug or a biologic. The drug may be a metabolite. In a preferred embodiment, the drug is suitable to be administered locally or regionally to a genitourinary tissue site, such as the urinary bladder or the prostate.

The excipient content may include essentially any pharmaceutically acceptable excipient known in the art. Representative examples of excipients include ingredients such as binders, lubricants, glidants, disintegrants, colors, fillers, viscosity modifiers, surface active agents, osmotic agents, diluents, coatings and preservatives, as well as other ingredients to facilitate handling, stability, dispersibility, wettability, release kinetics, manufacturing, storing, or administration of the drug.

In a preferred embodiment, the drug formulation is in a solid or semi-solid form in order to reduce the overall volume of the drug payload and thereby reduce the size of the device, facilitating its implantation, insertion, or deployment into a patient. In many embodiments, the drug formulation desirably includes no or a minimum quantity of excipient for the same reasons of volume/size minimization. The semi-solid form may be, for example, an emulsion or suspension; a gel or a paste. The solid form may be, for example, a tablet (e.g., mini-tablet), pellet, bead, powder, granules, capsule, or other solid drug unit.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base.

High solubility drugs may be suited for release due to an osmotic pressure gradient, such as via an aperture in the housing in communication with the drug reservoir, while low solubility drugs may be suited for release via diffusion, such as directly through the device wall or through one or more apertures or passing pores in the device wall. For example, lidocaine base may be released via diffusion through a silicone wall without an aperture. Thus, the drug may be formulated to have a high or low solubility depending on the intended release mode. In one embodiment, the drug is formulated to improve its apparent solubility in the environment of its use, such as its apparent solubility in urine within the bladder.

In one embodiment, the drug is for the treatment of pain. A variety of anesthetic agents, analgesic agents, and combinations thereof may be used. In embodiments, the device delivers one or more anesthetic agents. The anesthetic agent may be a cocaine analogue. In embodiments, the anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with an anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, and naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin.

In one embodiment, the drug delivery device is used in association with the placement of a ureteral stent, such as to treat pain, urinary urgency or urinary frequency resulting from ureteral stent placement. Non-limiting examples of specific drugs for such treatment include anti-muscarinics, beta-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, antimuscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, solifenacin, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In another embodiment, the drug delivery device is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may include a monoclonal antibody, a TNF inhibitor, an antileukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). The drug treatment may be coupled with a conventional radiation or surgical therapy targeted to the cancerous tissue.

Other cancer treatment drugs include small molecules, such as Apaziquone, adriamycin, AD-32, doxorubicin, docetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-α2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In another embodiment, the drug delivery device is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the drug delivery device is used to treat fibrosis of a genitourinary site, such as the bladder or uterus. Representative examples of drugs for the treatment of fibroids include pentoxphylline (xanthine analogue), anti-TNF, antiTGF agents, GnRH analogues, exogenous progestins, antiprogestins, selective estrogen receptor modulators, danazol and NSAIDs.

The drug delivery device also may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

As mentioned above, the drug formulation may be in solid form. In an embodiment, the drug formulation is in the form of one or more solid drug units, each unit being a solid, discrete object that substantially retains a selectively imparted shape (at the temperature and pressure conditions to which the delivery device normally will be exposed during assembly, storage, and handling before implantation, insertion, or deployment). The solid drug units may be in the form of a tablet, pellet, or bead, although other configurations are possible.

Drug tablets may be made by a direct compression tableting process, a molding process, or other processes known in the pharmaceutical arts. The tablets optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in vivo dissolution and drug release characteristics.

The individual drug units may have essentially any selected shape and dimension that fits within the drug reservoir lumen of the devices described herein. In one embodiment, the drug units are sized and shaped such that the drug reservoir lumen is substantially filled by a selected number of drug units. Each drug unit may have a cross-sectional shape that substantially corresponds to a cross-sectional shape of the drug reservoir lumen. For example, the drug units may be substantially cylindrical in shape for positioning in a substantially cylindrical drug reservoir lumen. Once loaded, the drug units can, in some embodiments, substantially fill the drug reservoir lumen.

In one embodiment, the solid drug units are shaped to align in a row when housed in the drug reservoir lumen. Each drug unit has a cross-sectional shape that corresponds to the cross-sectional shape of the drug reservoir lumen, and each drug unit may have end face shapes that correspond to the end faces of adjacent drug units. Thus, once the drug tablets are loaded in the drug reservoir lumen, the line or row of drug tablets may substantially fill the drug reservoir lumen with interstices or breaks formed between adjacent drug units. The interstices or breaks accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

In embodiments in which the solid drug units are designed for insertion or implantation in a lumen or cavity in the body, such as the bladder, via a drug delivery device, the drug units may be "mini-tablets" that are suitably sized and shaped for insertion through a natural lumen of the body, such as the urethra. For the purpose of this disclosure, the term "mini-tablet" generally indicates a solid drug unit that is substantially cylindrical in shape, having end faces and a side face that is substantially cylindrical. The mini-tablet has a diameter, extending along the end face, in the range of about 1.0 to about 3.2 mm, such as between about 1.5 and about 3.1 mm. The mini-tablet has a length, extending along the side face, in the range of about 1.7 mm to about 4.8 mm, such as between about 2.0 mm and about 4.5 mm.

In order to maximize the amount of drug that can be stored in and released from a given drug delivery device of a selected (small) size, the drug formulation preferably contains a high weight fraction of drug or API, with a reduced or low weight fraction of excipients as are required for manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a drug tablet that has 90% by weight of a drug in salt form may include less than 90% by weight of that drug in free base form.

In one embodiment, the drug formulation is more than 50% by weight drug. In a preferred embodiment, 75% or more of the weight of the drug formulation is drug, with the remainder of the weight being excipients, such as lubricants and binders that facilitate making the drug formulation, including a powder or tablet. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the drug formulation. In some cases, the drug content is about 75% or more of the weight of the drug formulation. More particularly, the drug content may be about 80% or more of the weight of the drug formulation. For example, the drug content may be between about 85% and about 99.9% of the weight of the drug formulation. In some embodiments, the excipient content can be omitted completely.

In one embodiment, the drug and excipients are selected and formulated to be water soluble, so that the drug formulation can be solubilized when the device is located within the urinary bladder or other tissue site, to release the solubilized drug.

In a preferred embodiment, the drug formulations are formulated to be sterilizable, either within or outside of the drug delivery device, without substantial or detrimental changes in the chemical or physical composition of the drug formulation. The drug formulation can be sterilized before or after loading/assembly into a drug delivery device, and the drug formulations possess a commercially reasonable shelf life. Once implanted, deployed, or inserted, the composition of the drug formulation is appropriate for the intended route of administration, is stable in acidic conditions, and provides pre-selected, reproducible drug release kinetics. For example, the drug formulation may be solubilized in the bladder to continuously release drug at a suitably stable rate drug over an extended period.

Although several drug formulations are described above as having a high weight fraction of drug or API and a low weight fraction of excipients, the drug formulations may have any weight fraction of drug, especially in cases in which the drug formulation includes a drug that is extremely potent, a stabilizing agent, or an agent that increases the solubility of the drug, among others or combinations thereof.

Elastic Retention Frame

As described above, some embodiments of the drug delivery device include an elastic retention frame, to bias the elongated body of the device into a coiled retention shape.

The elastic retention frame is operable to impart elasticity to the device structure, such that the device is elastically deformable between a retention shape and a relatively straightened shape. In one embodiment, the elastic retention frame is biased (i.e., naturally assumes) to have a coiled retention shape, and may be manipulated into the relatively straightened shape for insertion into the body, and then returns to the retention shape upon insertion into the bladder or other body cavity in a patient. The elastic retention frame in the relatively straightened shape may be shaped for insertion into the body through the working channel of a deployment instrument such as a catheter or cystoscope. To achieve this functionality, the elastic retention frame has an elastic limit, modulus, and/or spring constant selected to impede the device from assuming the relatively straightened shape once it is deployed in the patient. Such a configuration may limit or prevent accidental expulsion of the device from the body under expected forces. For example, the device may be retained in the bladder during urination or contraction of the detrusor muscle. Various examples of elastic retention frames are described in U.S. Patent Application Publication No. 2009/0149833 to Cima et al. and U.S. Pat. No. 8,679,094 to Cima et al., which are incorporated herein by reference.

The elastic retention frame may be formed of any elastic material effective to impart a suitable modulus or spring constant to the elongated body, and thus to the device. The elastic wire may be formed from a superelastic alloy, such as nitinol or another superelastic alloy.

In embodiments, the elastic retention frame may be in a form having a high enough spring constant to retain the device within a body cavity, such as the bladder. A high modulus material may be used, or a low modulus material. Especially when a low-modulus material is used, the elastic retention frame may have a diameter and/or shape that provide a spring constant without which the frame would significantly deform under the forces of urination. For example, the elastic retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m.

An elastic retention frame that assumes a pretzel shape may be relatively resistant to compressive forces. The pretzel shape essentially is formed of two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

Other Device Features

The drug delivery device may also include a retrieval string to facilitate withdrawal of a device from the patient, such as in cases in which the device is non-resorbable or otherwise needs to be removed. For example, the retrieval string may extend (or be selectively extendable) from the patient's urethra to facilitate manual removal of the device residing the patient's bladder.

In one embodiment, the device includes at least one radio-opaque portion or structure to facilitate detection or viewing (e.g., by X-ray imaging or fluoroscopy) of the device by a medical practitioner as part of the implantation, insertion, or retrieval procedure. In one embodiment, the device is constructed, at least in part, of a material that includes a radio-opaque filler material, such as barium sulfate or another radio-opaque material known in the art. Fluoroscopy may be used during deployment and/or retrieval of the device by providing accurate real-time imaging of the position and orientation of the device to the practitioner performing the procedure.

Use and Applications of the Drug Delivery Devices

In embodiments, the drug delivery devices described herein are used to administer one or more drugs to a patient in need thereof. Advantageously, the methods enable the local, continuous delivery of the one or more drugs into the body at therapeutically effective amounts over an extended period.

Generally, the methods of administering a drug to patient in need thereof include inserting into the patient the drug delivery device and permitting the drug to be released from the device. In certain embodiments, elution of drug from the device may occur following dissolution of the drug within the drug reservoir lumen. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

As used herein, the term "patient" refers primarily to a human adult or child, but also may include other suitable mammalian animals, for example in a pre-clinical trial or in veterinary care.

The device may be implanted, inserted, or deployed at any desired site, including in the urinary bladder or other body cavity or lumen of a patient in need thereof. The drug delivery devices provided herein also may be configured for subcutaneous, intramuscular, intraocular, intraperitoneal, and/or intrauterine implantation. Subsequently, the device may release one or more drugs for the treatment of one or more conditions, locally to one or more tissues at the deployment site and/or regionally to other tissues distal from the deployment site. Thereafter, the device may be retrieved, resorbed, excreted, or some combination thereof.

In some embodiments, the device is inserted into a patient by passing the drug delivery device through a deployment instrument and releasing the device from the deployment instrument into the body. For example, the device may be inserted into the patient by passing the device through the patient's urethra and into the patient's urinary bladder. In cases in which the device is inserted into a body cavity such as the bladder, the device assumes a retention shape once the device emerges from the deployment instrument into the cavity.

Once inserted, the device may release the drug, for example by osmotic pressure or diffusion through a wall structure of the device. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, 90, or 120 days, or more. In one embodiment, the drug is released continuously over a period from about 3 day to about 30 days in a therapeutically effective amount. The rate of delivery and dosage of the drug can be selected depending upon the drug being delivered and the disease or condition being treated.

In instances where the device is inserted into the bladder, the device may be deployed in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In an embodiment, the device is configured for intravesical insertion for use in the local administration of one or more drugs into the bladder to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In some embodiments, the drug delivery device is deployed into the bladder of a patient for regional drug delivery to one or more nearby genitourinary sites. The device may release drug locally to the bladder and regionally to other sites near the bladder. Such delivery may provide an alternative to systemic administration, which may entail undesirable side effects or result in insufficient bioavailability of the drug.

The present invention may be further understood with reference to the following non-limiting example.

Example

Figure 4A:
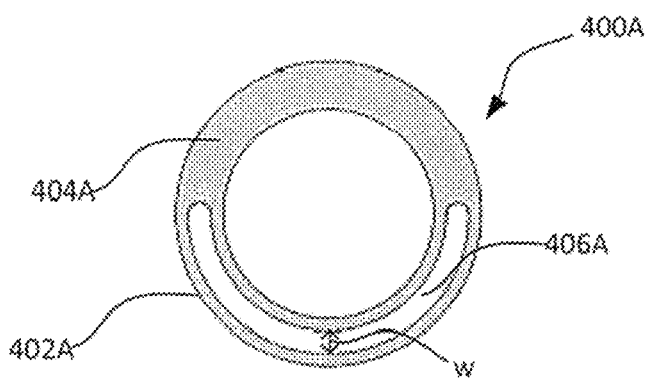
FIGS. 4A-4C are cross-sectional views of various annular drug housing designs used to assess water/drug permeation.
Figure 4B:
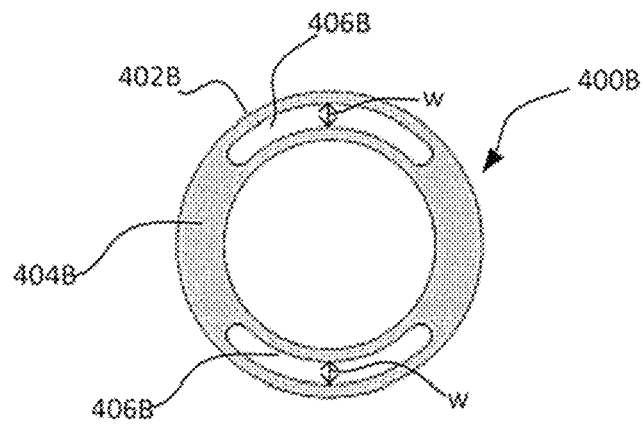
Figure 4C:
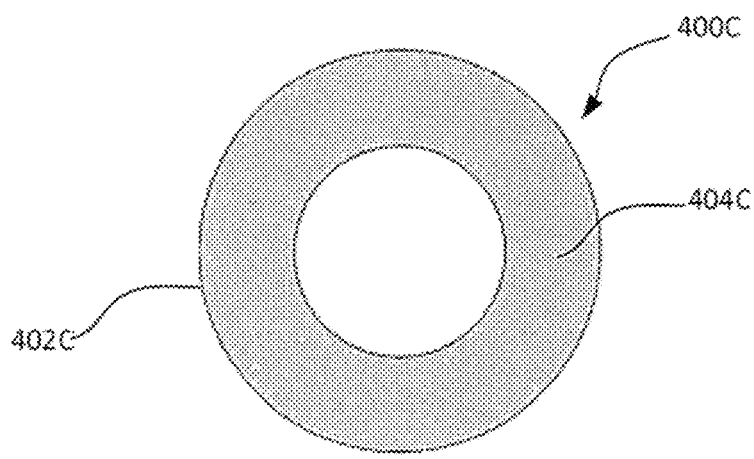

Three different devices, having the cross-sectional designs shown in FIGS. 4A-C, were designed to study how much drug or water can pass through the walls of the devices. The first device (device A) 400A and the second device (device B) 400B were designed to include an extruded tube 402A, 402B with an inner diameter of 2.6 mm, an outer diameter of 3.8 mm, and a wall thickness of 0.6 mm. The extruded tube 402A of device A included a single secondary lumen 406A within the tube wall 404A, and the extruded tube 402B of device B included two secondary lumens 406B within the tube wall 404B. The width, w, of each secondary lumen 406A, 406B was 0.28 mm. The third device (device C) 400C, which was designed for comparison purposes, included an extruded tube 402C with an inner diameter of 2.6 mm, an outer diameter of 5.0 mm, and a tube wall 404C thickness of 1.2 mm. Device C had no secondary lumen.

The permeable angle (i.e., the arc angle where no secondary lumen is present) was determined and thereafter the "Permeable Angle/Wall Thickness" index was calculated. The table below shows the same index for all three devices. Thus, although devices A and B 400A, 400B, are smaller in size, each would allow the same amount of water and/or drug to pass as through as larger device C 400C. These results indicated that the inclusion of one or more secondary lumens can achieve the similar effect as increasing wall thickness. Therefore the inclusion of secondary lumen beneficially could be used to retard the drug release rate in a relatively thin walled device.

TABLE

Experimental Device Design Parameters

| Device | Inner diameter (mm) | Outer diameter (mm) | Wall Thickness (mm) | Permeable Angle (degrees) | Permeable Angle/Wall Thickness Index |
| --- | --- | --- | --- | --- | --- |
| A | 2.64 | 3.84 | 0.6 | 180 | 300 |
| B | 2.64 | 3.84 | 0.6 | 180 (= 90 × 2) | 300 |
| C | 2.64 | 5.04 | 1.2 | 360 | 300 |

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

I claim:

1. A drug delivery device for controlled release of drug into the urinary bladder of a patient comprising:
    an elongated, elastic body extending between a closed first end and a closed second end, wherein the elastic body comprises a water permeable outer wall structure having a cylindrical shaped external surface extending between the first and second ends;
    an elongated hub structure located within, and coaxial with, the outer wall structure and extending between the first and second ends;
    two or more spoke structures extending between and connecting the outer wall structure and the hub structure, the spoke, outer wall, and hub structures defining at least one elongate drug reservoir lumen and at least one air lumen; and
    a drug payload disposed in the at least one drug reservoir lumen,
    wherein the device is elastically deformable between a relatively straightened shape suited for insertion of the device through a urethra and into the urinary bladder of the patient and a coiled retention shape which is suited to retain the device within the urinary bladder.

2. The device of claim 1, wherein the hub structure comprises an annulus in which the lumen of the annulus includes an elastic retention frame disposed therein, the elastic retention frame imparting the coiled retention shape to the device.

3. The device of claim 1, wherein the hub structure is shape set to impart the coiled retention shape to the device.

4. The device of claim 1, wherein the at least one air lumen is filled with a gas.

5. The device of claim 1, wherein the spoke, outer wall, and hub structures comprise silicone, a polyurethane, or a combination thereof.

6. The device of claim 1, wherein the drug payload is in a solid or semi-solid form.

7. The device of claim 6, wherein the device is operable in vivo to permit water to diffuse into the at least one drug reservoir lumen and solubilize the drug payload and to controllably release solubilized drug from the device by osmotic pressure.

8. The device of claim 7, wherein the outer wall structure, at a portion thereof defining the drug reservoir lumen, comprises an orifice for the release of the solubilized drug.

9. The device of claim 1, wherein the drug payload is the form of a plurality of tablets.

10. The device of claim 9, wherein the tablets are cylindrical and the at least one drug reservoir lumen is not cylindrical, such that open spaces are provided in the drug reservoir lumen between portions of the tablets and portions of the outer wall, spoke, and hub structures.

11. The device of claim 1, wherein the device is operable in vivo to permit water to diffuse into the at least one drug reservoir lumen and solubilize the drug payload and to controllably release solubilized drug from the device by diffusion.

12. The device of claim 1, which has exactly two spoke structures, the device having exactly one drug reservoir lumen and exactly one air lumen.

13. The device of claim 12, wherein the two spoke structures are positioned to define an obtuse angle bounding the drug reservoir lumen and a reflex angle bounding the air lumen.

14. The device of claim 1, which has exactly three spoke structures.

15. The device of claim 14, wherein the device has exactly one drug reservoir lumen and exactly two air lumen, and the three spoke structures are positioned to define an obtuse angle bounding each of the drug reservoir lumen and the two air lumen.

16. The device of claim 1, which the drug payload comprises a high solubility drug.

17. The device of claim 1, wherein the spoke, outer wall, and hub structures are coextruded and integrally connected.

18. A drug delivery device comprising:
    an elongated, elastic body extending between a first end and a second end, wherein the elastic body comprises a water permeable first wall structure having an external surface and an internal surface defining an elongated drug reservoir lumen extending between the first and second ends; and
    a drug payload disposed in the drug reservoir lumen,
    wherein the elastic body comprises a second wall structure which in part defines one or more secondary lumens extending between the first and second ends and located between the second wall structure and the first wall structure, wherein the one or more secondary lumens are effective to retard or prevent in vivo diffusion of (i) water into the drug reservoir lumen and/or (ii) solubilized drug out of the drug reservoir lumen,
    wherein the first wall structure comprises an annulus in which the drug reservoir lumen is the central lumen of the annulus.

19. The device of claim 18, wherein the one or more secondary lumens are filled with a gas.

20. The device of claim 18, wherein the one or more secondary lumens are filled with a diffusion-resistant polymeric material.

21. The device of claim 18, wherein the first or second wall structure further comprises a retention frame lumen in which an elastic retention frame is disposed.

22. The device of claim 18, wherein the first wall structure comprises silicone, a polyurethane, ethylene-vinyl acetate (EVA), or a combination thereof.

23. The device of claim 18, wherein the second wall structure comprises a high durometer silicone.

24. The device of claim 18, wherein the device is elastically deformable between a relatively straightened shape suited for insertion of the device through a urethra and into the urinary bladder of a patient and a coiled retention shape which is suited to retain the device within the urinary bladder.

25. The device of claim 18, wherein the drug payload is in a solid or semi-solid form.

26. The device of claim 25, wherein the device is operable in vivo to permit water to diffuse into the drug reservoir lumen and solubilize the drug payload and to controllably release solubilized drug from the device by osmotic pressure.

27. The device of claim 25, wherein the device is operable in vivo to permit water to diffuse into the drug reservoir lumen and solubilize the drug payload and to controllably release solubilized drug from the device by diffusion through the first wall structure.

28. The device of claim 18, wherein the drug payload is the form of a plurality of tablets.

29. The device of claim 18, wherein:
    the first wall structure is an elongated, extruded tube having two separate lumen, which consist of the drug reservoir lumen and a retention frame lumen, and
    the second wall structure is an elongated, extruded C-shaped tube segment connected to, and offset to one side of, the first wall structure.

30. The device of claim 29, wherein the drug reservoir lumen has a circular cross-sectional shape and the secondary lumen has a non-circular cross-sectional shape.

31. The device of claim 29, wherein the first and second wall structures are coextruded and integrally connected.

* * * * *